United States Patent
Takase

(10) Patent No.: US 9,765,097 B2
(45) Date of Patent: Sep. 19, 2017

(54) METHOD FOR PRODUCING SILANE COMPOUND HAVING SULFONYL BOND

(71) Applicant: NISSAN CHEMICAL INDUSTRIES, LTD., Tokyo (JP)

(72) Inventor: Kenji Takase, Toyama (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/321,384

(22) PCT Filed: Jun. 17, 2015

(86) PCT No.: PCT/JP2015/067483
§ 371 (c)(1),
(2) Date: Dec. 22, 2016

(87) PCT Pub. No.: WO2015/198945
PCT Pub. Date: Dec. 30, 2015

(65) Prior Publication Data
US 2017/0158716 A1 Jun. 8, 2017

(30) Foreign Application Priority Data

Jun. 23, 2014 (JP) .................... 2014-128284

(51) Int. Cl.
*C07F 7/04* (2006.01)
*C07F 7/18* (2006.01)
(52) U.S. Cl.
CPC .................. *C07F 7/1892* (2013.01)
(58) Field of Classification Search
CPC ...................................... C07F 7/1892
USPC ....................................... 556/428
See application file for complete search history.

(56) References Cited

U.S. PATENT DOCUMENTS 5,008,369 A * 4/1991 Robello ............... C08G 75/20
528/388

\* cited by examiner

*Primary Examiner* — Sudhakar Katakam
*Assistant Examiner* — Kofi Adzamli

(74) *Attorney, Agent, or Firm* — Oliff PLC

(57) ABSTRACT

A method of producing a silane compound having a Formula (1) sulfonyl bond includes reacting a Formula (I) chlorosulfonyl compound with sodium sulfite in water as a solvent in the presence of a base, to produce a Formula (II) sulfinic acid sodium salt: and adding an aromatic hydrocarbon solvent to carry out azeotropic dehydration, and adding an aprotic polar solvent and a Formula (III) chloroalkylsilane compound.

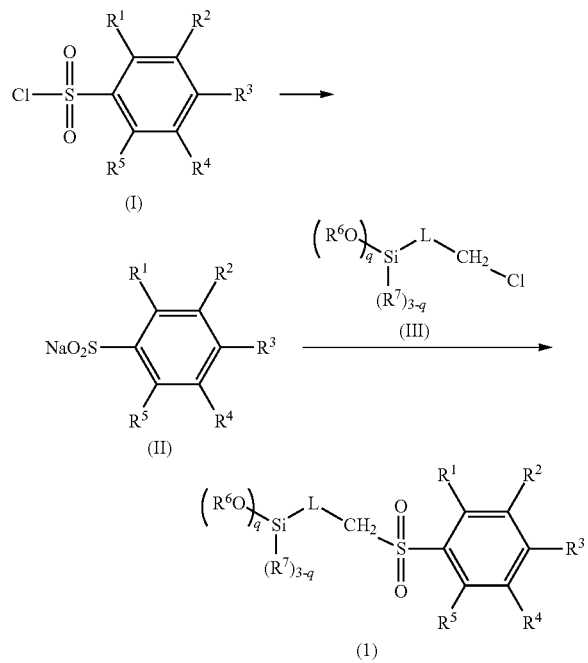

(wherein $R^1$, $R^2$, $R^3$, $R^4$, and $R^5$ are each independently a substituent selected from a hydrogen atom, halogen atom, alkyl group, alkoxy group, haloalkyl group, haloalkoxy group, cyano group, and nitro group, $R^2$ and $R^1$ or $R^3$ may form —CH=CH—CH=CH— together, $R^6$ and $R^7$ are each independently a $C_{1-5}$ alkyl group, L is a single bond or saturated or unsaturated divalent $C_{1-19}$ hydrocarbon group having a linear, branched, cyclic structure, or a combination thereof, and q is an integer of 1 to 3).

5 Claims, No Drawings

METHOD FOR PRODUCING SILANE COMPOUND HAVING SULFONYL BOND

TECHNICAL FIELD

The present invention relates to a novel method for producing a silane compound having a sulfonyl bond useful for a raw material for a composition for forming an underlayer film between a substrate and a resist (such as a photoresist, an electron beam resist, and an EUV resist) used in production of a semiconductor device.

BACKGROUND ART

Fine processing by lithography using a photoresist has been conventionally carried out in production of a semiconductor device. The fine processing is a processing method in which a thin film of the photoresist is formed on a semiconductor substrate such as a silicon wafer, irradiated with an active light such as ultraviolet light through a mask pattern that has a pattern of the semiconductor device, and developed, and the substrate is etched using the obtained photoresist pattern as a protective film to form fine concaves and convexes corresponding to the pattern on a surface of the substrate. In recent years, an increase in degree of integration of the semiconductor device has advanced, and shorter wavelength active light tends to be used from a KrF excimer laser (248 nm) to an ArF excimer laser (193 nm) or EUV light (13.5 nm). For this reason, influence of reflection of active light from the semiconductor substrate is a sever problem.

As an underlayer film between a semiconductor substrate and a photoresist, a film that contains silicon or the like and is conventionally known as a hard mask has been used (for example, see Patent Document 1). In this case, constituent components of the resist and the hard mask (underlayer film) are largely different. Therefore, rates of removing the constituent components by dry etching largely depend on the type of gas used in the dry etching. When the type of gas is appropriately selected, only the hard mask can be selectively removed by dry etching without a large decrease in the film thickness of the photoresist.

In the recent production of a semiconductor device, a resist underlayer film is disposed between the semiconductor substrate and the photoresist in order to achieve various effects including an effect of preventing the reflection. Although a composition for the resist underlayer film has been investigated, development of a novel material for the resist underlayer film is desired to meet diverse properties that the resist underlayer film is required to have.

In such a circumstance, a resist underlayer film formed from a resist underlayer film-forming composition containing a polyorganosiloxane obtained using a constant amount of silane compound having a sulfonyl bond improves the dry etching rate relative to a resist as an upper layer and has resistance to dry etching during processing a substrate, and the shape of a resist pattern after exposure and development is a rectangular. It has recently been found that the composition allows substrate processing using a fine pattern (see Patent Document 2).

PRIOR ART DOCUMENTS

Patent Documents

Patent Document 1: International Publication No. 2011/033965 (WO 2011/033965)

Patent Document 2: International Publication No. WO 2013/022099 (WO 2013/022099)

SUMMARY OF THE INVENTION

Problem to be Solved by the Invention

Conventionally, a silane compound having a sulfonyl bond described in Patent Document 2 is produced by a reaction of sodium organosulfinate with haloalkyl trialkoxysilane. However, this method has such a defect that sodium organosulfinate as a raw material is not easily available.

If sodium organosulfinate can be produced from an organosulfonic acid chloride as a raw material that is a general-purpose material easily obtained from organosulfonic acid, it is expected that the silane compound having a sulfonyl bond as a target is produced at low cost by a reaction of the sodium organosulfinate with haloalkyl trialkoxysilane.

Unfortunately, a desired compound cannot be obtained. This is because a reaction system of producing the sodium organosulfinate from the organosulfonic acid chloride is carried out in water, and at the subsequent reaction with haloalkyl trialkoxysilane, a condensation reaction of trialkoxysilane with water remained in the system may occur.

An object of the present invention is to provide a novel method for producing a silane compound having a sulfonyl bond useful for a raw material for a resist underlayer film to solve the aforementioned problems.

Means for Solving the Problems

A first aspect of the invention of the present application is a method for producing a silane compound having a sulfonyl bond of Formula (1):

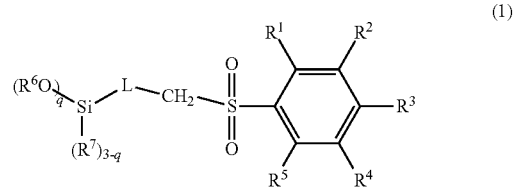

(wherein $R^1$, $R^2$, $R^3$, $R^4$, and $R^5$ are each independently a substituent selected from the group consisting of a hydrogen atom, a halogen atom, a $C_{1-10}$ alkyl group, a $C_{1-10}$ alkoxy group, a $C_{1-10}$ haloalkyl group, a $C_{1-10}$ haloalkoxy group, a cyano group, and a nitro group, $R^2$ and $R^1$ or $R^3$ may form —CH=CH—CH=CH— together, $R^6$ and $R^7$ are each independently a $C_{1-5}$ alkyl group, L is a single bond or a saturated or unsaturated divalent $C_{1-19}$ hydrocarbon group having a structure that is linear, branched, cyclic, or a combination thereof, and q is an integer of 1 to 3.), the method comprising a step (A) of reacting a chlorosulfonyl compound of Formula (I):

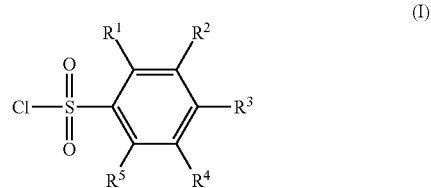

(wherein $R^1$, $R^2$, $R^3$, $R^4$, and $R^5$ mean the same as above) with sodium sulfite in water as a solvent in the presence of a base to produce a sulfinic acid sodium salt of Formula (II):

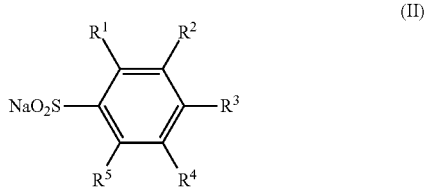

(II)

(wherein $R^1$, $R^2$, $R^3$, $R^4$, and $R^5$ mean the same as above) and a step (B) of adding an aromatic hydrocarbon solvent to this reaction system to carry out azeotropic dehydration, and adding an aprotic polar solvent and a chloroalkylsilane compound of Formula (III):

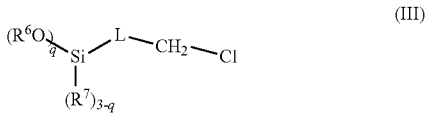

(III)

(wherein $R^6$, $R^7$, L, and q mean the same as above) to cause a reaction.

A second aspect is the method according to the first aspect, wherein at the step (B), the reaction after addition of the aprotic polar solvent is carried out while the aromatic hydrocarbon solvent in the reaction system is distilled off.

A third aspect is the method according to the first or second aspect, wherein the aprotic polar solvent is N-methyl-2-pyrrolidone.

A fourth aspect is the method according to the first aspect, wherein $R^1$, $R^2$, $R^3$, $R^4$, and $R^5$ are each independently a hydrogen atom, a halogen atom, a $C_{1-10}$ alkyl group, a $C_{1-10}$ alkoxy group, a $C_{1-10}$ haloalkyl group, or a $C_{1-10}$ haloalkoxy group.

Effects of the Invention

According to the method of the present invention, a silane compound having a sulfonyl bond useful as a raw material for a resist underlayer film can be efficiently produced from an easily available and inexpensive raw material while production of a byproduct and a side reaction are suppressed.

MODES FOR CARRYING OUT THE INVENTION

In the method of the present invention, a chlorosulfonyl compound of Formula (I) is reacted with sodium sulfite in water as a solvent in the presence of a base, to produce a sulfinic acid sodium salt of Formula (II), an aromatic hydrocarbon solvent is added to this reaction system to carry out azeotropic dehydration, and an aprotic polar solvent and a chloroalkylsilane compound of Formula (III) are added to cause a reaction. Thus, a silane compound having a sulfonyl bond of Formula (1) can be obtained.

Especially, after production of the sulfinic acid sodium salt of Formula (II), water as a solvent that exists in the system is replaced by the aromatic hydrocarbon solvent by azeotropic dehydration. After that, the aromatic hydrocarbon solvent is distilled off and replaced by the aprotic polar solvent, and at the same time, the chloroalkylsilane compound of Formula (III) is reacted with the sulfinic acid sodium salt. As a result, production of a byproduct and occurrence of a side reaction such as condensation are suppressed, and a target compound is obtained at relatively high purity. Based on this finding, the present invention is made.

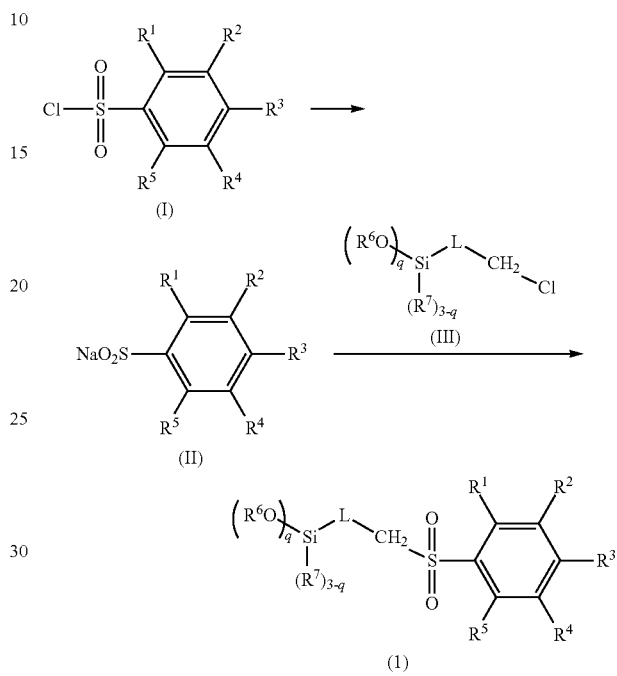

In aforementioned Formulae (1), (I), (II), and (III), $R^1$, $R^2$, $R^3$, $R^4$, and $R^5$ are each independently a substituent selected from the group consisting of a hydrogen atom, a halogen atom, a $C_{1-10}$ alkyl group, a $C_{1-10}$ alkoxy group, a $C_{1-10}$ haloalkyl group, a $C_{1-10}$ haloalkoxy group, a cyano group, and a nitro group, $R^2$ and $R^1$ or $R^3$ may form —CH=CH—CH=CH— together, $R^6$ and $R^7$ are each independently a $C_{1-5}$ alkyl group, L is a single bond or a saturated or unsaturated divalent $C_{1-19}$ hydrocarbon group having a structure that is linear, branched, cyclic, or a combination thereof, and q is an integer of 1 to 3.

In a hydrolyzable organosilane of Formula (1) of the present invention, specific examples of each of $R^1$, $R^2$, $R^3$, $R^4$, and $R^5$ independently include a hydrogen atom, a fluorine atom, a chlorine atom, a bromine atom, an iodine atom, methyl group, ethyl group, n-propyl group, i-propyl group, cyclopropyl group, n-butyl group, i-butyl group, s-butyl group, t-butyl group, cyclobutyl group, n-pentyl group, cyclopentyl group, n-hexyl group, cyclohexyl group, trifluoromethyl group, methoxy group, ethoxy group, n-propyloxy group, i-propyloxy group, n-butyloxy group, i-butyloxy group, s-butyloxy group, t-butyloxy group, n-pentyloxy group, cyclopentyloxy group, n-hexyloxy group, cyclohexyloxy group, cyano group, and nitro group. Furthermore, $R^2$ and $R^1$ or $R^3$ may form —CH=CH—CH=CH— together.

In the hydrolyzable organosilane of Formula (1) of the present invention, examples of $R^6$ include methyl group, ethyl group, n-propyl group, i-propyl group, cyclopropyl group, n-butyl group, i-butyl group, s-butyl group, t-butyl group, cyclobutyl group, n-pentyl group, and cyclopentyl group. In particular, methyl group and ethyl group are preferred.

In the hydrolyzable organosilane of Formula (1) of the present invention, examples of $R^7$ include methyl group, ethyl group, n-propyl group, i-propyl group, cyclopropyl group, n-butyl group, i-butyl group, s-butyl group, t-butyl group, cyclobutyl group, n-pentyl group, and cyclopentyl group. In particular, methyl group and ethyl group are preferred.

In the hydrolyzable organosilane of Formula (1) of the present invention, L is a single bond or, for example, a divalent group (alkylene group) obtained by removing one hydrogen atom from an alkyl group selected from methyl group, ethyl group, n-propyl group, i-propyl group, n-butyl group, i-butyl group, s-butyl group, t-butyl group, n-pentyl group, 1-methyl-n-butyl group, 2-methyl-n-butyl group, 3-methyl-n-butyl group, 1,1-dimethyl-n-propyl group, 1,2-dimethyl-n-propyl group, 2,2-dimethyl-n-propyl group, 1-ethyl-n-propyl group, n-hexyl group, 1-methyl-n-pentyl group, 2-methyl-n-pentyl group, 3-methyl-n-pentyl group, 4-methyl-n-pentyl group, 1,1-dimethyl-n-butyl group, 1,2-dimethyl-n-butyl group, 1,3-dimethyl-n-butyl group, 2,2-dimethyl-n-butyl group, 2,3-dimethyl-n-butyl group, 3,3-dimethyl-n-butyl group, 1-ethyl-n-butyl group, 2-ethyl-n-butyl group, 1,1,2-trimethyl-n-propyl group, 1,2,2-trimethyl-n-propyl group, 1-ethyl-1-methyl-n-propyl group, 1-ethyl-2-methyl-n-propyl group, n-heptyl group, 1-methyl-n-hexyl group, 2-methyl-n-hexyl group, 3-methyl-n-hexyl group, 1,1-dimethyl-n-pentyl group, 1,2-dimethyl-n-pentyl group, 1,3-dimethyl-n-pentyl group, 2,2-dimethyl-n-pentyl group, 2,3-dimethyl-n-pentyl group, 3,3-dimethyl-n-pentyl group, 1-ethyl-n-pentyl group, 2-ethyl-n-pentyl group, 3-ethyl-n-pentyl group, 1-methyl-1-ethyl-n-butyl group, 1-methyl-2-ethyl-n-butyl group, 1-ethyl-2-methyl-n-butyl group, 2-methyl-2-ethyl-n-butyl group, 2-ethyl-3-methyl-n-butyl group, n-octyl group, 1-methyl-n-heptyl group, 2-methyl-n-heptyl group, 3-methyl-n-heptyl group, 1,1-dimethyl-n-hexyl group, 1,2-dimethyl-n-hexyl group, 1,3-dimethyl-n-hexyl group, 2,2-dimethyl-n-hexyl group, 2,3-dimethyl-n-hexyl group, 3,3-dimethyl-n-hexyl group, 1-ethyl-n-hexyl group, 2-ethyl-n-hexyl group, 3-ethyl-n-hexyl group, 1-methyl-1-ethyl-n-pentyl group, 1-methyl-2-ethyl-n-pentyl group, 1-methyl-3-ethyl-n-pentyl group, 2-methyl-2-ethyl-n-pentyl group, 2-methyl-3-ethyl-n-pentyl group, 3-methyl-3-ethyl-n-pentyl group, n-nonyl group, and n-decyl group, o-phenylene group, m-phenylene group, p-phenylene group, or a group obtained by substituting one or more methylene groups in the alkylene group with an o-phenylene group, an m-phenylene group, or a p-phenylene group.

Among them, ethylene group, p-phenylene group, and a single bond are preferred.

In the hydrolyzable organosilane of Formula (1) of the present invention, q is an integer of 1 to 3.

[Step (A): Reaction of Compound of Formula (I) into Compound of Formula (II)]

In the reaction in which the chlorosulfonyl compound of Formula (I) is reacted with sodium sulfite in water as a solvent in the presence of a base to produce the sulfinic acid sodium salt of Formula (II) (reaction of (I) into (II)), the amount of sodium sulfite used is preferably 0.9 equivalent weights to 3.0 equivalent weights, and more preferably 1.0 equivalent weight to 1.5 equivalent weights, relative to 1 equivalent weight of the compound of Formula (I).

The amount (reaction concentration) of water used as a reaction solvent is not particularly limited. Water may be used in an amount of 0.1 to 100 times the mass of the chlorosulfonyl compound of Formula (I). The amount is preferably 1 to 10 times, and more preferably 2 to 5 times the mass of the chlorosulfonyl compound.

The reaction temperature is not particularly limited, and is, for example, 1 to 100° C., preferably 10 to 90° C., and more preferably 50° C. to 80° C.

The reaction time is typically 0.05 to 200 hours, and preferably 0.5 to 100 hours.

Examples of the base used in the reaction of (I) into (II) include inorganic bases including: alkali metal hydroxides such as sodium hydroxide and potassium hydroxide; alkali metal carbonates such as sodium carbonate and potassium carbonate; alkali metal bicarbonates such as sodium bicarbonate and potassium bicarbonate; and alkali metal salts of inorganic acid such as 2- or 3-sodium phosphate and 2- or 3-potassium phosphate.

The amount of the base used may be 2 to 10 mol, preferably 2 to 6 mol, and more preferably 2.5 to 5 mol, relative to 1 mol of the chlorosulfonyl compound of Formula (I).

This reaction may be carried out under normal pressure or under pressure. The reaction may be carried out in a batch-wise or continuous manner.

After the reaction, a separation operation is carried out by adding an organic solvent and water, and an organic phase is concentrated and dried under reduced pressure. Thus, the sulfinic acid sodium salt of Formula (II) as a target compound is obtained.

As described below in the present invention, after water as a solvent is distilled off by azeotropic dehydration and replaced by the aromatic hydrocarbon solvent, the aromatic hydrocarbon solvent is distilled off and replaced by the aprotic polar solvent, and at substantially the same time, a reaction of the sulfinic acid sodium salt of Formula (II) with the chloroalkylsilane compound of Formula (III) advances. As a result, the compound of Formula (1) can be obtained at high purity in one pot from a starting material.

[Step (B): Reaction of Compound of Formula (II) into Compound of Formula (1)]

After completion of the reaction of (I) into (II), water as a solvent is distilled off from the reaction system by azeotropic dehydration, and replaced by the aromatic hydrocarbon solvent selected from benzene, toluene, and the like, the aprotic polar solvent and the chloroalkylsilane compound of Formula (III) are added to cause the reaction of the compound of Formula (II) with the compound of Formula (III). It is preferable that the reaction of the compound of Formula (II) with the compound of Formula (III) be carried out while the aromatic hydrocarbon solvent is distilled off in the reaction system. Thus, the silane compound having a sulfonyl bond of Formula (1) can be obtained.

The amount of the aromatic hydrocarbon solvent added in azeotropic dehydration is 0.8 to 10 times, preferably 1 to 5 times, and more preferably 1 to 2 times the mass of water present in the reaction system. It is preferable that the azeotropic dehydration be carried out in a reactor provided with a Dean-Stark apparatus under heating and reflux.

After water is completely distilled off in the reaction system and replacing by the aromatic hydrocarbon solvent is completed, the aprotic polar solvent and the chloroalkylsilane compound of Formula (III) are added to the reaction system, to cause a reaction.

Examples of the aprotic polar solvent include N-methyl-2-pyrrolidone, N,N-dimethylformamide, N,N-dimethylacetamide, and 1,3-dimethyl-2-imidazolidinone. N-methyl-2-pyrrolidone is particularly preferred.

The amount of the aprotic polar solvent added at that time is 0.1 to 100 times, preferably 1 to 10 times, and more preferably 2 to 5 times the mass of the chlorosulfonyl compound of Formula (I) as the starting material.

The amount of the chloroalkylsilane compound of Formula (III) added is 0.4 to 0.99 mol, preferably 0.5 to 0.8 mol, and more preferably 0.6 to 0.7 mol relative to 1 mol of the chlorosulfonyl compound of Formula (I) as the starting material.

In the reaction after addition of the aprotic polar solvent and the chloroalkylsilane compound of Formula (III) in the reaction system, the reaction temperature is preferably 160° C. or lower. Heating at higher than 160° C. is not preferred since a side reaction occurs.

The reaction time is typically 0.05 to 200 hours, and preferably 0.5 to 100 hours.

As described above, the reaction after addition of the aprotic polar solvent and the chloroalkylsilane compound of Formula (III) to the reaction system is carried out while the aromatic hydrocarbon solvent is distilled off in the reaction system. Specifically, while the aromatic hydrocarbon solvent is replaced by the aprotic polar solvent, the reaction of the compound of Formula (II) with the compound of Formula (III) advances. This is preferred since the reaction rate can be accelerated and production of a byproduct and a side reaction can be suppressed.

The aromatic hydrocarbon solvent can be distilled off even under normal pressure or reduced pressure.

The temperature at which the aromatic hydrocarbon solvent is distilled off is equal to or higher than the boiling point of the aromatic hydrocarbon solvent, and preferably 160° C. or lower. Heating at higher than 160° C. is not preferred since a side reaction occurs.

In order to efficiently promote the reaction of (II) with (III), an iodide such as tetra-n-butylammonium iodide, sodium iodide, and potassium iodide may be added.

The reaction liquid is cooled to room temperature, and solution separation is carried out by adding an organic solvent that is separated from water and water. Thus, a crude product of the compound of Formula (1) is obtained. The resulting crude product is purified by distillation, to obtain the compound of Formula (1).

Examples of the hydrolyzable organosilane of (1) include as follows. In the following Formulae, Me is methyl group, and Et is ethyl group.

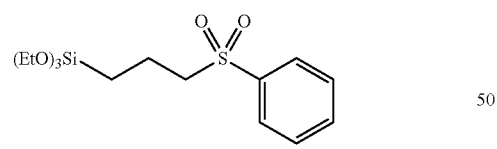

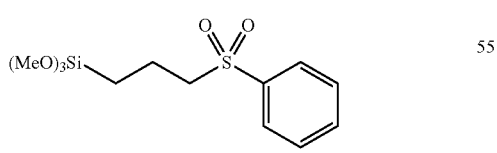

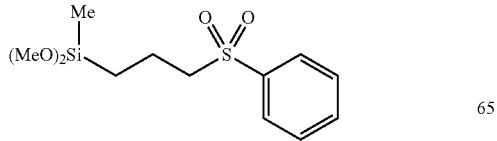

-continued

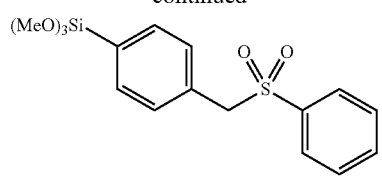

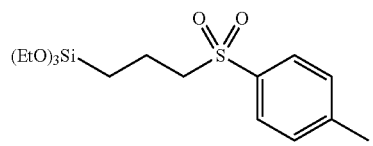

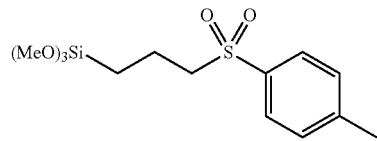

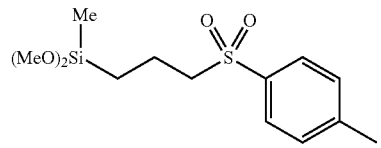

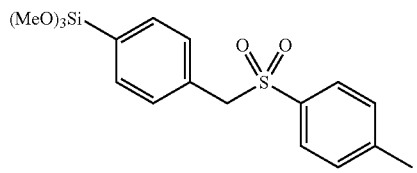

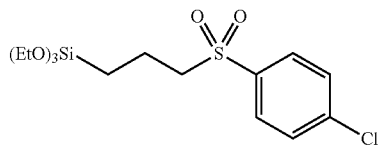

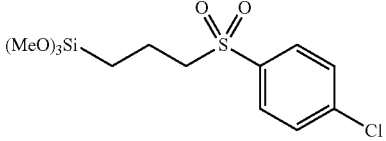

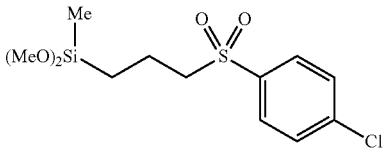

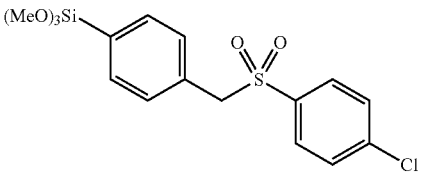

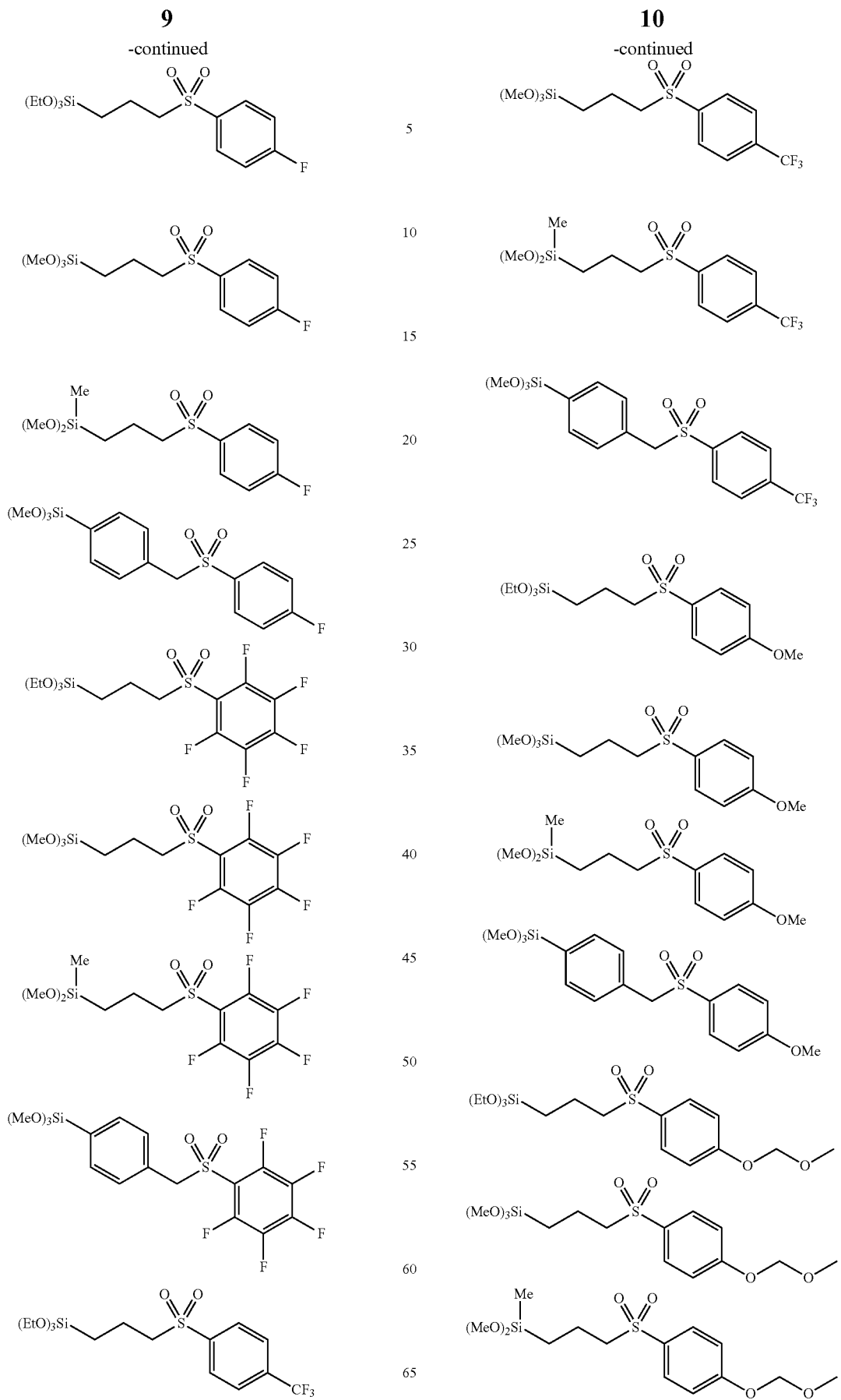

11
-continued

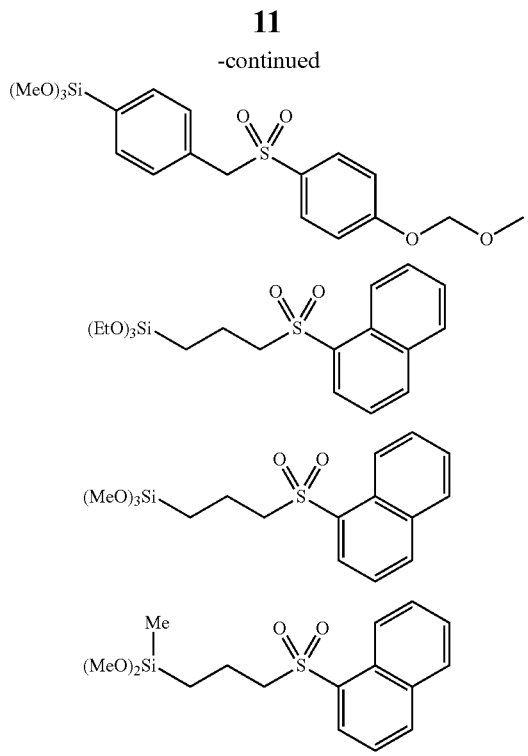

12
-continued

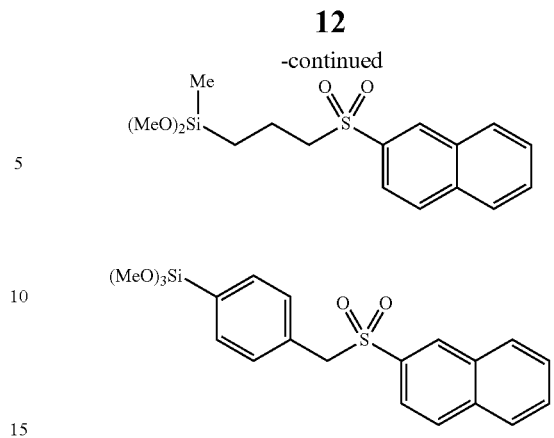

Hereinafter, the present invention will be more specifically described with reference to Examples, but the present invention is not limited to the Examples.

EXAMPLES

Example 1 Production of Compound 1

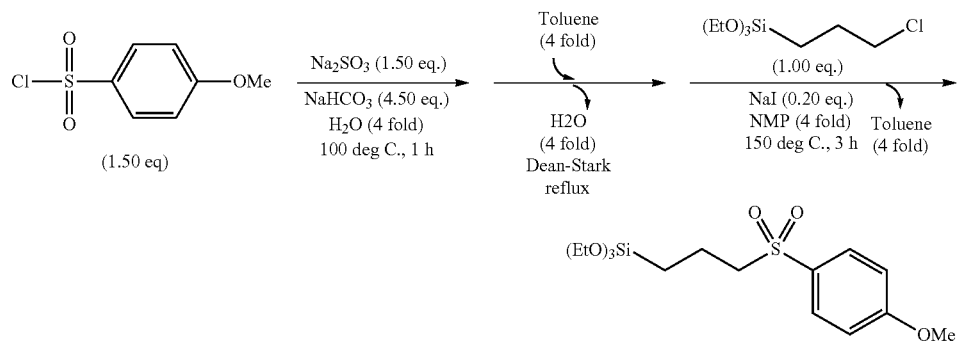

-continued

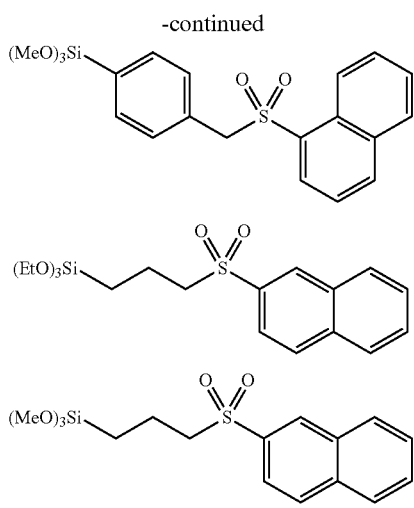

32.2 g (0.156 mol) of 4-methoxybenzene-1-sulfonyl chloride, 19.6 g (0.156 mol) of sodium sulfite, 39.3 g (0.467 mol) of sodium bicarbonate, and 100 g of water were placed in a 500-mL recovery flask, and heated to 100° C., and a reaction was caused for 1 hour. Subsequently, 100 g of toluene was added, the mixture was heated until a reflux state, and water was collected by a Dean-Stark apparatus. 25.0 g (0.104 mol) of 3-chloropropyltriethoxysilane, 3.1 g (0.021 mol) of sodium iodide, and 100 g of N-methyl-2-pyrrolidone were further added, and the mixture was stirred under heating for 3 hours while the solvent was distilled off at 150° C. The reaction liquid was separated using toluene and water, activated carbon was added to the organic phase, the organic phase was stirred and filtered, and toluene was removed by an evaporator, to obtain a crude product. The crude product was distilled under reduced pressure, to obtain a compound 1 as a target at a yield of 24%.

$^1$H-NMR (500 MHz, DMSO-d$_6$): 0.63 ppm (m, 2H), 1.10 ppm (t, 9H), 1.55 ppm (m, 2H), 3.24 ppm (m, 2H), 3.71 ppm (m, 6H), 3.86 ppm (s, 3H), 7.17 ppm (d, 2H), 7.79 ppm (d, 2H)

Example 2 Production of Compound 2

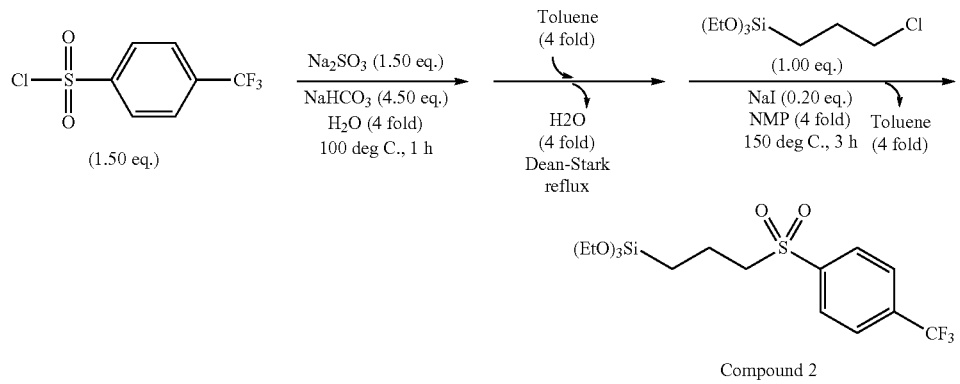

Compound 2

38.1 g (0.156 mol) of 4-trifluoromethylbenzene-1-sulfonyl chloride, 19.6 g (0.156 mol) of sodium sulfite, 39.3 g (0.467 mol) of sodium bicarbonate, and 100 g of water were placed in a 500-mL recovery flask, and heated to 100° C., and a reaction was caused for 1 hour. Subsequently, 100 g of toluene was added, the mixture was heated until a reflux state, and water was collected by a Dean-Stark apparatus. 25.0 g (0.104 mol) of 3-chloropropyltriethoxysilane, 3.1 g (0.021 mol) of sodium iodide, and 100 g of N-methyl-2-pyrrolidone were further added, and the mixture was stirred under heating for 3 hours while the solvent was distilled off at 150° C. The reaction liquid was separated using toluene and water, activated carbon was added to the organic phase, the organic phase was stirred and filtered, and toluene was removed by an evaporator, to obtain a crude product. The crude product was distilled under reduced pressure, to obtain a compound 2 as a target at a yield of 46%.

$^1$H-NMR (500 MHz, DMSO-d$_6$): 0.64 ppm (m, 2H), 1.09 ppm (t, 9H), 1.58 ppm (m, 2H), 3.43 ppm (m, 2H), 3.68 ppm (m, 6H), 8.07 ppm (d, 2H), 8.12 ppm (d, 2H)

Example 3 Production of Compound 3

24.25 g (0.125 mol) of 4-fluorobenzene-1-sulfonyl chloride, 15.7 g (0.125 mol) of sodium sulfite, 31.4 g (0.374 mol) of sodium bicarbonate, and 100 g of water were placed in a 500-mL recovery flask, and heated to 100° C., and a reaction was caused for 1 hour. Subsequently, 100 g of toluene was added, the mixture was heated until a reflux state, and water was collected by a Dean-Stark apparatus. 20.0 g (0.083 mol) of 3-chloropropyltriethoxysilane, 2.5 g (0.017 mol) of sodium iodide, and 100 g of N-methyl-2-pyrrolidone were further added, and the mixture was stirred under heating for 3 hours while the solvent was distilled off at 150° C. The reaction liquid was separated using toluene and water, activated carbon was added to the organic phase, the organic phase was stirred and filtered, and toluene was removed by an evaporator, to obtain a crude product. The crude product was distilled under reduced pressure, to obtain a compound 3 as a target at a yield of 28%.

$^1$H-NMR (500 MHz, DMSO-d$_6$): 0.63 ppm (m, 2H), 1.10 ppm (t, 9H), 1.58 ppm (m, 2H), 3.33 ppm (m, 2H), 3.69 ppm (m, 6H), 7.52 ppm (d, 2H), 7.95 ppm (d, 2H)

INDUSTRIAL APPLICABILITY

According to the method of the present invention, a silane compound having a sulfonyl bond usable as a resist underlayer film-forming composition for lithography for forming a resist underlayer film that can be used as a hard mask can be easily obtained. When the silane compound having a sulfonyl bond obtained by the present invention is used as a component of the resist underlayer film-forming composi-

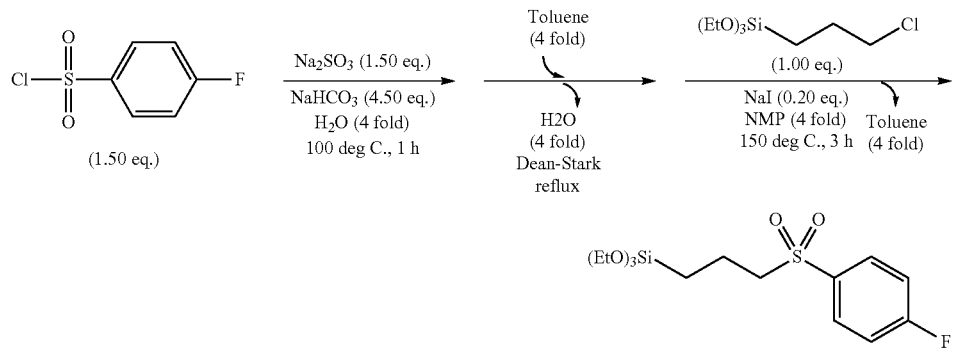

Compound 3 tion, a resist underlayer film that does not cause intermixing with a top coating resist can be formed. The dry etching rate of the resist underlayer film when a fluorine-based etching gas is used is higher than that of the resist. Therefore, a resist pattern can be transferred to the resist underlayer film. The resist underlayer film exhibits resistance to etching when an oxygen-based etching gas is used. Therefore, the resist pattern transferred to the resist underlayer film can be transferred to an organic underlayer film formed on a lower layer of the resist underlayer film. Therefore, a silane compound having a sulfonyl bond that is important to provide a resist underlayer film-forming composition for forming a resist underlayer film capable of substrate processing using a rectangular pattern can be provided by the method of the present invention.

The invention claimed is:

1. A method for producing a silane compound having a sulfonyl bond of Formula (1):

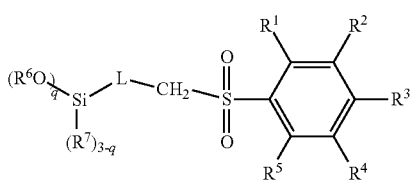

(1)

(wherein $R^1$, $R^2$, $R^3$, $R^4$, and $R^5$ are each independently a substituent selected from the group consisting of a hydrogen atom, a halogen atom, a $C_{1-10}$ alkyl group, a $C_{1-10}$ alkoxy group, a $C_{1-10}$ haloalkyl group, a $C_{1-10}$ haloalkoxy group, a cyano group, and a nitro group, $R^2$ and $R^1$ or $R^3$ may form —CH=CH—CH=CH— together, $R^6$ and $R^7$ are each independently a $C_{1-5}$ alkyl group, L is a single bond or a saturated or unsaturated divalent $C_{1-19}$ hydrocarbon group having a structure that is linear, branched, cyclic, or a combination thereof, and q is an integer of 1 to 3), and the method comprising the steps of:

a step (A) of reacting a chlorosulfonyl compound of Formula (I):

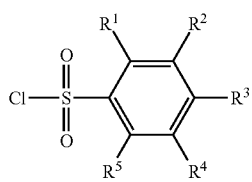

(I)

(wherein $R^1$, $R^2$, $R^3$, $R^4$, and $R^5$ mean the same as above) with sodium sulfite in water as a solvent in the presence of a base to produce a sulfinic acid sodium salt of Formula (II):

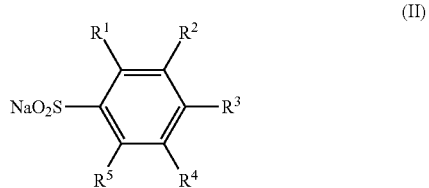

(II)

(wherein $R^1$, $R^2$, $R^3$, $R^4$, and $R^5$ mean the same as above); and a step (B) of adding an aromatic hydrocarbon solvent to this reaction system to carry out azeotropic dehydration, and adding an aprotic polar solvent and a chloroalkylsilane compound of Formula (III):

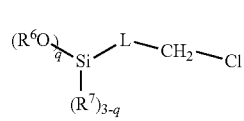

(III)

(wherein $R^6$, $R^7$, L, and q mean the same as above) to cause a reaction.

2. The method according to claim 1, wherein at the step (B), the reaction after addition of the aprotic polar solvent is carried out while the aromatic hydrocarbon solvent in the reaction system is distilled off.

3. The method according to claim 1, wherein the aprotic polar solvent is N-methyl-2-pyrrolidone.

4. The method according to claim 1, wherein $R^1$, $R^2$, $R^3$, $R^4$, and $R^5$ are each independently a hydrogen atom, a halogen atom, a $C_{1-10}$ alkyl group, a $C_{1-10}$ alkoxy group, a $C_{1-10}$ haloalkyl group, or a $C_{1-10}$ haloalkoxy group.

5. The method according to claim 2, wherein the aprotic polar solvent is N-methyl-2-pyrrolidone.

* * * * *